(12) United States Patent
Innocenzi et al.

(10) Patent No.: US 11,471,296 B2
(45) Date of Patent: Oct. 18, 2022

(54) PARTIAL ENDOPROSTHESIS DEVICE FOR A VERTEBRAL JOINT

(71) Applicants: Gualtiero Innocenzi, Rome (IT); Piero Petrini, Città di Castello (IT); G & G S.R.L., Florence (IT)

(72) Inventors: Gualtiero Innocenzi, Rome (IT); Piero Petrini, Città di Castello (IT); Giancarlo Guizzardi, Florence (IT)

(73) Assignee: G & G S.R.L., Florence (IT)

( * ) Notice: Subject to any disclaimer, the term of this patent is extended or adjusted under 35 U.S.C. 154(b) by 0 days.

(21) Appl. No.: 16/954,985

(22) PCT Filed: Dec. 18, 2018

(86) PCT No.: PCT/IB2018/060291
§ 371 (c)(1),
(2) Date: Jun. 17, 2020

(87) PCT Pub. No.: WO2019/123281
PCT Pub. Date: Jun. 27, 2019

(65) Prior Publication Data
US 2021/0022880 A1    Jan. 28, 2021

(30) Foreign Application Priority Data
Dec. 18, 2017   (IT) .................. 102017000146043

(51) Int. Cl.
*A61F 2/44* (2006.01)
*A61F 2/00* (2006.01)
*A61F 2/30* (2006.01)

(52) U.S. Cl.
CPC .... *A61F 2/4405* (2013.01); *A61F 2002/0081* (2013.01); *A61F 2002/3093* (2013.01);
(Continued)

(58) Field of Classification Search
CPC .......... A61F 2/44; A61F 2/442; A61F 2/4405; A61F 2002/0081; A61F 2002/30774; A61F 2002/3093
See application file for complete search history.

(56) References Cited

U.S. PATENT DOCUMENTS 7,517,358 B2 *  4/2009  Petersen ............... A61F 2/4405
                                                        606/246
7,744,630 B2 *  6/2010  Lancial ................. A61F 2/4405
                                                        606/247
(Continued)

FOREIGN PATENT DOCUMENTS

| IT | UA20 164 453 A1 | 12/2017 |
| WO | 2007/070785 A1 | 6/2007 |
| WO | 2014/042388 A2 | 3/2014 |

*Primary Examiner* — Christopher D. Prone
(74) *Attorney, Agent, or Firm* — Maschoff Brennan

(57) ABSTRACT

A partial endoprosthesis device preserves the motion of a vertebral joint for implant into a spinal segment and includes an articular portion having a thickness that increases in the direction of introduction between the articular facets. The articular portion is elongated along a longitudinal axis with a opposite first and second faces. The first face has a central protrusion that is configured so that, by implanting the device with the articular portion inserted between an upper articular facet of a lower vertebra and a corresponding lower articular facet of upper vertebra adjacent to the lower vertebra, and with the first face in contact with either the upper or lower articular facet, and with the second face in contact with the other articular facet, the articular portion, with the first face, pushes against the first articular facet and finally becomes integral by osteointegration with the lower articular facet.

19 Claims, 4 Drawing Sheets

(52) U.S. Cl.
CPC ............... *A61F 2002/30774* (2013.01); *A61F 2310/00023* (2013.01)

(56) References Cited

U.S. PATENT DOCUMENTS

| | | | |
|---|---|---|---|
| 8,672,972 B2* | 3/2014 | Erickson | A61B 17/7032 606/246 |
| 9,622,874 B2* | 4/2017 | McCormack | A61F 2/4611 |
| 2005/0159746 A1* | 7/2005 | Grob | A61B 17/7064 606/247 |
| 2007/0055373 A1 | 3/2007 | Hudgins et al. | |
| 2007/0135814 A1* | 6/2007 | Farris | A61B 17/7064 606/279 |
| 2009/0036927 A1 | 2/2009 | Vestgaarden | |
| 2010/0121378 A1* | 5/2010 | Malek | A61B 17/7064 606/247 |
| 2011/0288556 A1 | 11/2011 | Winslow et al. | |
| 2012/0277801 A1* | 11/2012 | Marik | A61F 2/4405 606/279 |
| 2013/0274882 A1 | 10/2013 | Guizzardi et al. | |
| 2017/0105767 A1 | 4/2017 | Blain | |

* cited by examiner

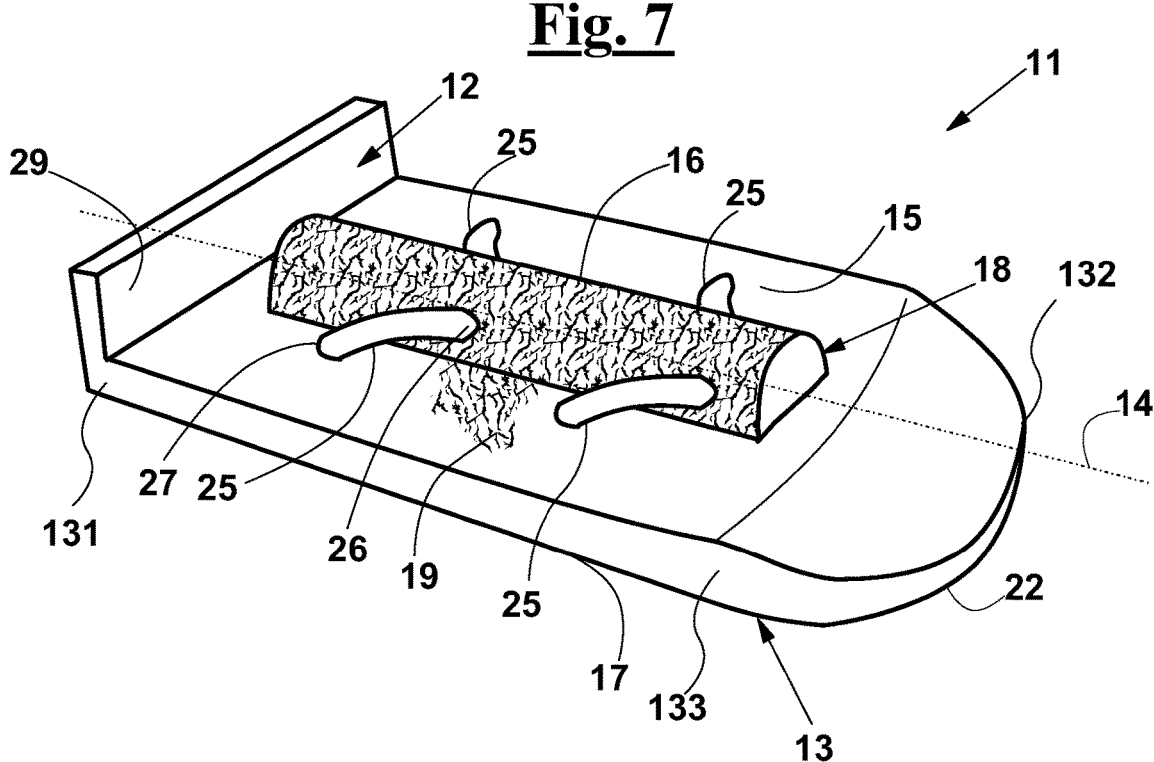
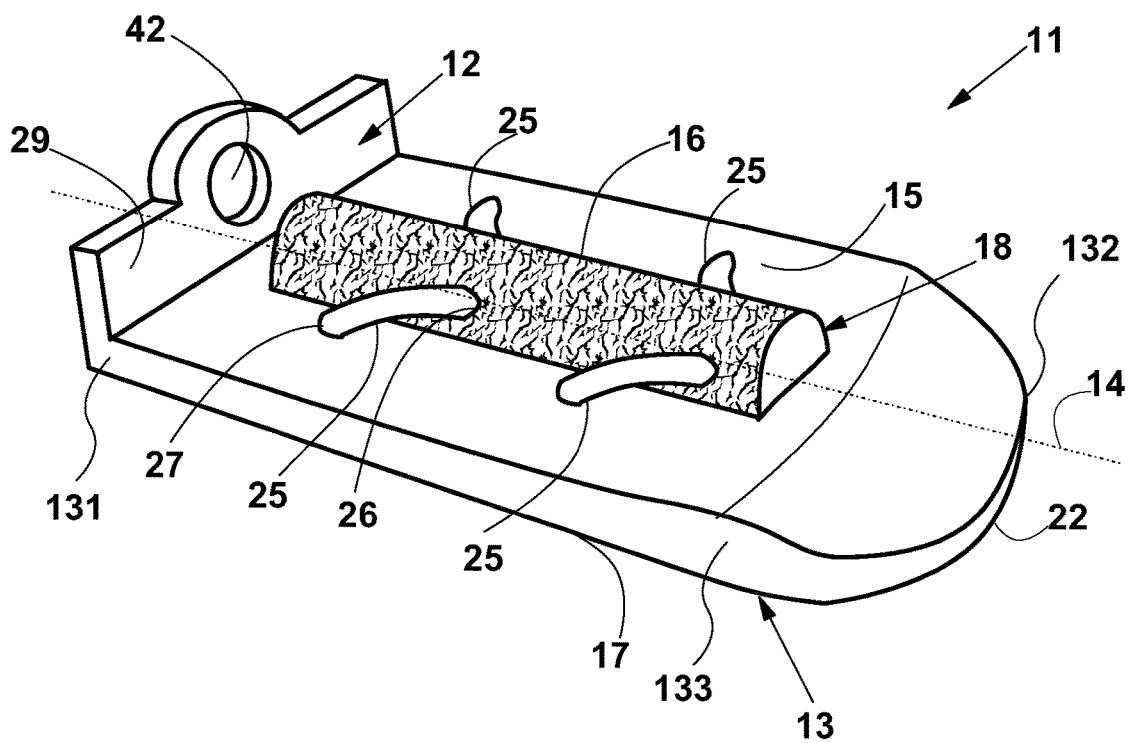

PARTIAL ENDOPROSTHESIS DEVICE FOR A VERTEBRAL JOINT

FIELD OF THE INVENTION

The present invention relates to a partial endoprosthesis device for a cervical intervertebral joint.

The device is suitable for treating patients suffering from a painful condition due to an early facet or disc degeneration with incipient foraminal stenosis, while preserving the relative movement of two adjacent vertebrae.

BACKGROUND OF THE INVENTION

As well known, most vertebral painful conditions are caused by the state of a joint, i.e. they depend on a relative motion deficit of the articular facets. This is case, in particular, for most neck pains.

The existing devices for treating these vertebral painful conditions can briefly classified into fusion devices for two or more adjacent vertebrae suppressing the relative motion thereof and, on the other hand, devices conceived to maintain the relative motion. Normally, the devices for preserving the relative motion are intersomatic devices, in particular they comprise disc replacement elements. In practice, only intersomatic devices exist for treating cervical spine painful conditions, of course, apart from the vertebral fusion devices.

In the case of the cervical vertebrae, the only currently available motion preservation intersomatic devices are implanted via anterior approaches. In fact, an intersomatic space cannot be reached via a posterior or lateral approach without running the risks of damaging nerve plexuses, which has severe neurological consequences for the patient. These risks are less important for non-cervical spinal levels and, therefore, rear approaches to the intersomatic space are preferred in those cases.

However, risks of neurological injuries and serious postoperative consequences are in any case involved if an anterior approach is used, which is required for implanting an intersomatic device at the cervical level.

US2011/288556 describes a partial endoprosthesis of an intervertebral joint, comprising a plate for introduction between the articular facets of two adjacent vertebrae. In order to maintain the device in the implant location before it becomes integrated with the bone, i.e. in order to primarily stabilize the device, screws are provided to fasten the device to the external surfaces of the laminae. This solution can damage and weaken the articular processes, in particular in the case of a cervical vertebra, since they are thin.

WO2014/042388 describes a device for spacing two adjacent vertebrae, configured to rigidly connect the vertebral bodies of two adjacent vertebrae to each other. In an embodiment, the device comprises a sawtooth-shaped primary stabilization means. This device is conceived for introduction between vertebral bodies, and is not suitable either for fixing two cervical facets to each other, or for preserving their relative movement, due to the sawtooth-shaped primary stabilization means, and would be also detrimental for the stability of the facets same.

WO2007/070785 describes a spacer device for restoring a physiologic distance between two articular facets of respective adjacent vertebrae, comprising a section, indicated as the intermediate section, whose size is suitable for introduction between the facets, and preferably also comprising a fastening portion configured to receive a mounting member like a screw for connection to the vertebral body. In an exemplary embodiment, the device is configured for connection to a single vertebral body of the two adjacent vertebrae. Even this device provides screws as the primary stabilization means, and involves therefore the above-mentioned drawbacks.

Further devices for at least partially preserving the relative movement of adjacent vertebrae and, in particular, of adjacent cervical vertebrae, are described in US 2013/274882 A1, US 2011/288556 A1, US 2005/159746 A1, US 2007/055373 A1.

SUMMARY OF THE INVENTION

It is therefore a feature of the present invention to provide a partial endoprosthesis of a cervical intervertebral joint, i.e. a device for implant in an articular process to functionally replace an articular facet of a cervical or cervical-adjacent vertebra, which provides a reliable primary stabilization before the device becomes integrated with the articular process.

It is also a feature of the invention to provide such a device that preserves the stability of the thin articular processes in which it becomes integrated, thus overcoming the problems of the above-cited prior art.

It is a particular feature of the invention to provide such a device that can be implanted by a relatively easy and not modestly invasive procedure.

It is also a feature of the invention to provide such a device and system that is easy and quick to be manufactured.

These and other objects are achieved by a partial endoprosthesis device as defined by independent claim No. 1. Exemplary specific embodiments of the invention are defined by the claims depending thereon.

According to the invention, a partial endoprosthesis device is provided for preserving the motion of a vertebral joint, for implant into a spinal segment comprising two adjacent vertebrae, wherein at least one of the two adjacent vertebrae is a cervical vertebra, the adjacent vertebrae comprising a lower vertebra having a couple of upper articular processes with respective upper articular facets and an upper vertebra having a couple of lower articular processes with respective lower articular facets, each upper articular facet of the lower vertebra articulated with a corresponding lower articular facet of the upper vertebra, the device comprising:
- an elongated articular portion extending along a longitudinal axis between a first end and a second end axially opposite to each other, the articular portion having a first face and a second face opposite to the first face, wherein the first face comprises a central protrusion having a height, with respect to the face, set between 0.5 mm and 3 mm, preferably between 1.5 and 2.5 mm, and having a surface made of an osteointegrable material;
- wherein the second face has a surface roughness Ra lower than 0.2 µm, wherein the first face has a plurality of primary stabilization elements,
- a shoulder portion adjacent to the first end and arranged at an angle with respect to the articular portion at a side opposite to the second face;

such that, by implanting the device:
- with the articular portion inserted between an upper articular facet of the upper articular facets of the lower vertebra and a corresponding lower articular facet of the upper vertebra, and
- with the first face in contact with a first articular facet selected between the upper articular facet and the lower articular facet, and with the second face in contact with a second articular facet selected between the lower articular facet and the upper articular facet, according to whether the upper articular facet or the lower articular facet is selected as the first articular facet, respectively, it is obtained that the articular portion, with its first face, finally becomes integral with the first articular facet by osteointegration and, with its second face, slidingly engages with the second articular facet so as to preserve the motion thereof, thus providing the partial endoprosthesis, wherein the main features of the device are that:
the articular portion has a thickness increasing from the first end going towards an own second end,
the primary stabilization elements are elongated and flexible elements;
the stabilization elements extend laterally with respect to the protrusion, between an own first connection end for connecting with the protrusion, and an own free end, and form an acute angle with the direction of the longitudinal axis, said angle oriented towards the first end of the articular portion.

Therefore, a primary stabilization means is provided that does not have the drawbacks described in the cited prior art, first of all it doesn't waken the structure of the thin articular processes of the cervical vertebrae, and the structure of the vertebral arch, which occurs, on the contrary, if screws are used.

This way, the primary stabilization elements provided as elongated and flexible elements, and oriented at an acute angle, due to their elongated shape and to their flexibility, can become closer to the protrusion while the device is being introduced into the articular space between the articular facets, and this way they do not hinder this introduction. Moreover, the elongated and flexible elements, once the device has been positioned, are fastened to the articular process like hooks, and resist against expulsion of the device from the articular space. In this fastening process, the thickness increase of the articular portion from the first end towards the second end cooperates with those elements, which creates a positive engagement between the articular portion and the articular facets engaged with one another. This active cooperation between the increasing thickness of the articular portion and the flexible primary stabilization means effectively restricts any possibility for the articular portion to be expelled from the space between the articular facets, in particular, during the implantation and the primary stabilization, before the articular process becomes integrated with the protrusion and the first face by osteosynthesis.

More in detail, the device is arranged with the protrusion comprising the osteointegrable surface in a recess suitably created by the surgeon in the first facet, which is the one to be functionally replaced. This recess is deep enough to allow the protrusion of the device to come into contact with a bleeding bone portion of the corresponding articular process, or in any case with a bone portion close to the trabecular portion, so as to assist the integration between the device and the bone. The protrusion is high enough to reach this inner portion of the articular process. On the other hand, the face opposite to the one bearing the protrusion is completely smooth, and allows the device to physiologically slide on the second facet, facing the first one, as if this second face were the patient's natural bone joint surface.

Therefore, the invention provides a prosthesis device for a joint surface, i.e. a device that can functionally replace a damaged bone joint surface of one of two adjacent vertebrae, at one cervical level or at a level adjacent thereto, and that solves the primary stabilization problems affecting the prior art. In other words, a device is obtained that provides a slidable prosthesis of the articular processes of two adjacent vertebrae, so as to heal such a condition as articular cartilage degeneration, while preserving the physiologic motion of the vertebrae and also restoring the natural foramen height. Due to articular degeneration, the foramen height decreases, causing stenosis. Moreover, said device is free from the above-mentioned prior art primary stabilization problems.

Preferably, the acute angle formed between the stabilization elements and the direction of the longitudinal axis of the articular portion, in a undeformed configuration, is set between 30° and 60°. Such an angle allows a good trade-off between a relative ease of insertion of the device into the articular space, and a grip of the primary stabilization means strong enough to effectively contrast the expulsion of the device from its implant location.

Advantageously, the primary stabilization elements, in an undeformed configuration, have a curvature with respect to a line between the connection end and the free end. Preferably, the primary stabilization elements have a convexity oriented towards the protrusion. Such a conformation improves the effectiveness of the primary stabilization elements, according to the invention, besides assisting bending during the introduction thereof.

In an exemplary embodiment, the primary stabilization elements are arranged symmetrically with respect to the longitudinal axis of the articular portion.

In particular, the surface roughness Ra of the second face is lower than 0.1 µm, more in particular, the surface roughness Ra is lower than 0.05 µm and, even more in particular, is lower than 0.025 µm.

Advantageously, the protrusion has a substantially uniform height over the first face.

The protrusion can have different forms along the longitudinal axis. In particular, it can have a semicylindrical shape, a prismatic shape or a combination thereof. The protrusion can also be manufactured in the form in more separate segments oriented along the longitudinal axis, in particular two or three segments can be provided. In particular, the protrusion can extend up to the shoulder portion.

In an exemplary embodiment, the protrusion can be hollow, i.e. it can a have a shell shape, like a cylindrical shell shape, or a box-like shape, these shapes defining a recess above a covered portion of the first face. This recess can be filled with bone material such as bank bone material, in order to assist osteointegration.

An osteointegrable material can also be arranged on portions of the first face different from the protrusion, besides the material arranged on the protrusion. In other words, the first face can comprise a further surface that has an osteointegrable material, this further surface adjacent to the protrusion. In particular, this further surface exposing osteointegrable material can extend to the whole first face, out of the protrusion. This way, further surface is provided for osteointegration of the device, which can take place at the side portions of the facets, provided these portions are prepared by removing the cartilage.

In order to assist osteointegration, the surface comprising the osteointegrable material of the first face can be a porous surface, or a corrugated surface, or in any case a surface having a surface roughness Ra higher than 0.2 µm.

Advantageously, the osteointegrable material is selected among titanium and titanium alloys. Preferably, the osteointegrable material comprises trabecular titanium, which is normally in a porous form.

The thickness of the articular portion is preferably set between 0.5 mm and 3.5 mm, more preferably between 1 mm and 3 mm and, in particular, between 1 mm and 2 mm, in order to be suitable for any specific size of the articular processes. Moreover, regardless of such values, the thickness of the articular portion at a maximum thickness portion is higher than the thickness at the first end by an amount set between 0.5 and 0.7 mm. The maximum thickness portion can be the second end portion or a zone adjacent or proximate thereto. This thickness difference is useful to cause the shape of the articular portion to better collaborate with the primary stabilization means.

The articular portion has a maximum length and a maximum width along and across the longitudinal axis, respectively, these dimensions preferably set between 8 mm and 15 mm, independently from each other, more preferably set between 10 mm and 14 mm, in particular between 10 mm and 12 mm. Even in this case, these size ranges make it possible to fit the device to any specific size of the articular processes and facets. In particular, the articular portion has a rectangular shape whose width and length are the above maximum sizes. As an alternative, the articular portion has a transversal side, at its second end portion, which can have a rounded shape, and/or can be tapered in height, between the second end and the maximum thickness portion, in order to assist the introduction into the articular space.

Advantageously, the articular portion has a width narrower than one half the width of the articular portion, preferably the width of the protrusion is set between $1/10$ and $4/10$ the width of the articular portion. This increases the mechanical stress physiologically arising in the articular process region at which the protrusion is inserted, which promotes osteointegration.

The second face comprises a material selected from the group consisting of:
Titanium, or a Titanium alloy;
a ceramic material;
a glass material.

Accordingly, the second face of the articular portion exposes a material, in particular titanium or an alloy thereof, smooth enough to assist the articular portion to relatively slide, by the second face of the device, on the second facet, i.e. on the upper articular facet of the lower vertebra or on the lower articular facet of the upper vertebra, thus maintaining the relative twist motion of the two adjacent vertebrae, which is associated with this relative sliding. The primary stabilization portion is preferably configured to abut against an external portion of the vertebra surrounding the articular space.

Advantageously, the shoulder portion has fastening means for fastening a percutaneous positioning device. In particular, the fastening means can comprise a screw-threaded hole.

A posterior or posterolateral or lateral approach can be used so as to more easily implant the device than via an anterior approach, which must be used to safely implant the conventional prior art devices.

BRIEF DESCRIPTION OF THE DRAWINGS

The invention will be now shown with the description of exemplary embodiments thereof, exemplifying but not limitative, with reference to the attached drawings, in which.

FIG. 7 shows a device according to an exemplary embodiment of the invention, in which the osteointegrable material is arranged on at least one part of the first face, besides the protrusion;
FIG. 8 shows a device according to an exemplary embodiment of the invention, in which the shoulder portion has fastening means comprising a screw-threaded hole, for fastening a percutaneous positioning device.

DESCRIPTION OF A PREFERRED EXEMPLARY EMBODIMENT

Figure 1:
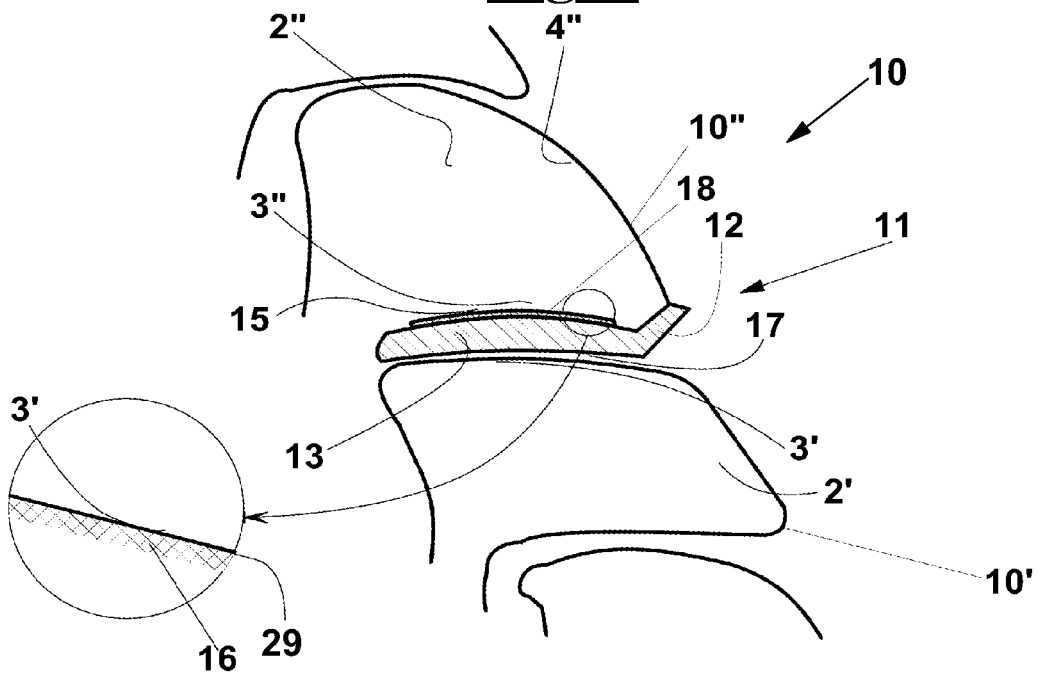
FIG. 1 is a cross sectional view of the device of FIG. 1, which is arranged to form a partial endoprosthesis of the joints between two adjacent vertebrae.

Exemplary embodiments of the partial endoprosthesis device according to the invention are described hereinafter. The device can be implanted into an articular space at a cervical level or at a cervical-adjacent level. This device replaces a bone joint surface that has been damaged, for instance by arthrosis, of one of two adjacent vertebrae, typically, but not exclusively of the upper vertebra, as shown in the drawings. The invention makes it possible to treat some vertebral diseases while preserving the relative mobility of the adjacent vertebrae defining the articular space.

Figure 2:
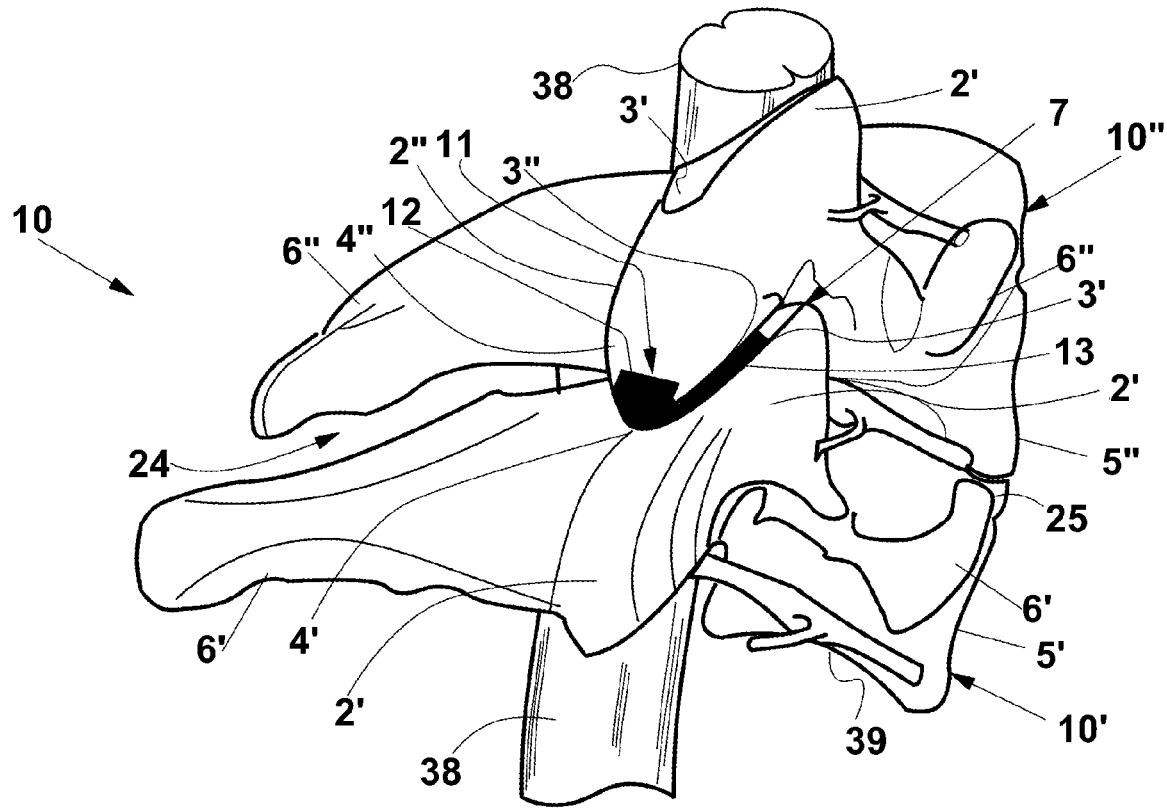
FIG. 2 is a perspective view of a segment of cervical spine, in which the device of FIG. 1 forms right and left articular endoprosthesis.

The anatomical references are indicated in FIGS. 1 and 2, which show a spinal segment 10 comprising two lower 10' and upper 10" adjacent cervical vertebrae. Vertebral bodies 5',5" of lower 10' and upper 10" vertebrae, respectively, are shown. Behind vertebral bodies 5,5", portions of the vertebral arches are shown, in particular the laminae 4',4" and, next to them, the articular processes 2',2" of cervical vertebrae 10',10". These include upper articular processes 2' of lower vertebra 10', each having an upper articular facet 3' at its upper end, and lower articular processes 2" of upper vertebra 10", each having a lower articular facet 3" at its lower end. Each upper articular facet 3' slidingly engages with a respective lower articular facet 3", defining an articular space 7 that contains a cartilaginous tissue, not shown. Moreover, the spinous processes 6',6" and the transverse processes 9',9" are shown of lower vertebra 10' and of upper vertebra 10", respectively.

Moreover, FIGS. 1 and 2 diagrammatically show a device 11, according to the invention, positioned between an upper articular facet 3' of lower vertebra 10' and a lower articular facet 3" of upper vertebra 10", in an exemplary embodiment, described hereinafter, in which device 11 has a shoulder portion 12 that, in this case, abuts against a portion of upper vertebra 10".

In the exemplary embodiment of FIG. 8, shoulder portion 12 has fastening means for fastening a percutaneous positioning device, in particular this fastening means comprises a screw-threaded hole 42.

Figure 3:
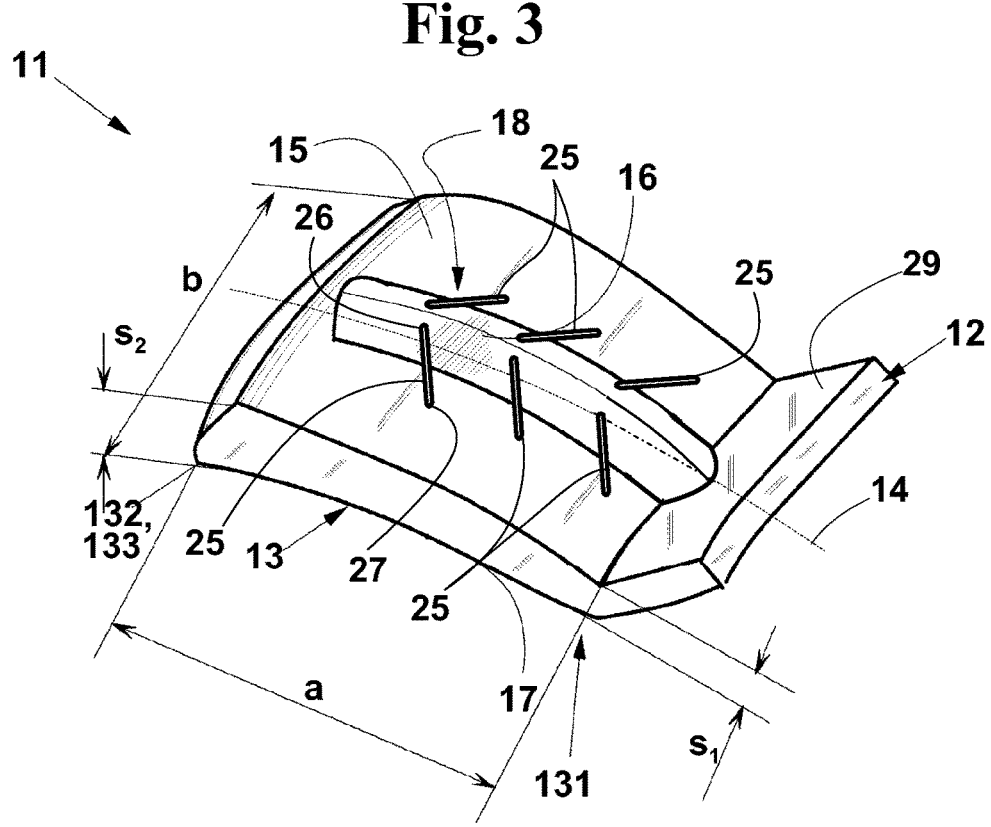
FIGS. 3 and 4 are perspective views of devices according to the invention, configured to be implanted between two adjacent vertebrae at a cervical level or at a cervical-adjacent level.
Figure 4:
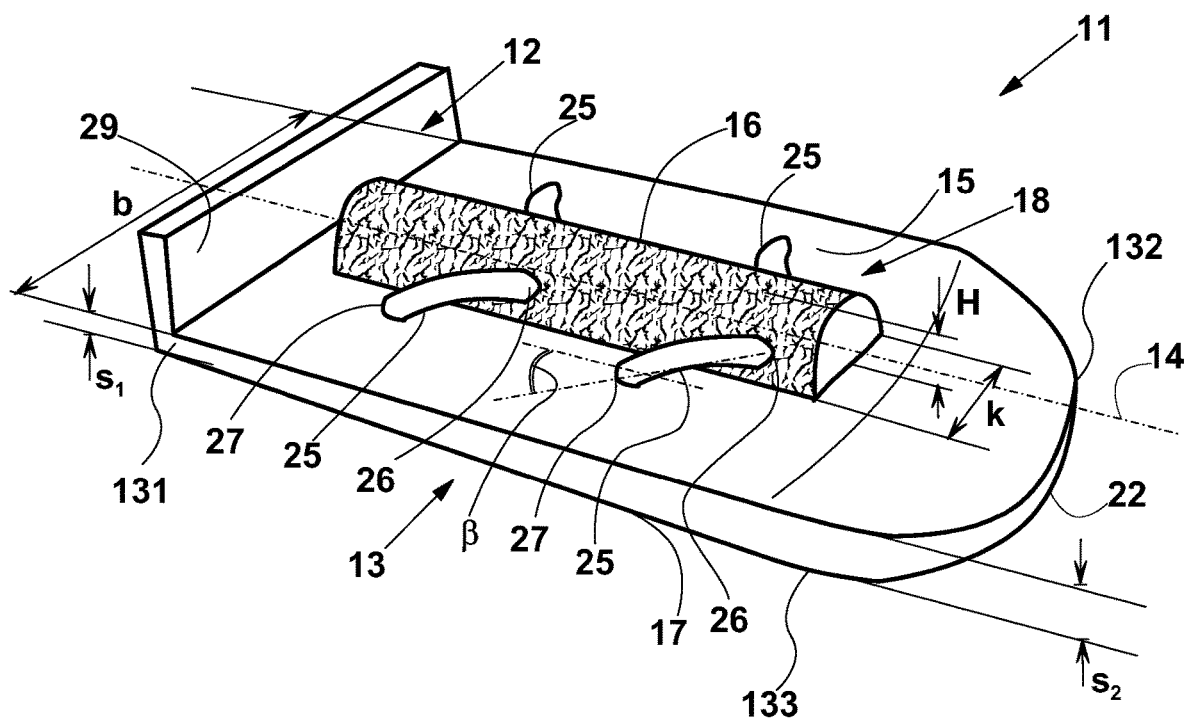
Figure 5:
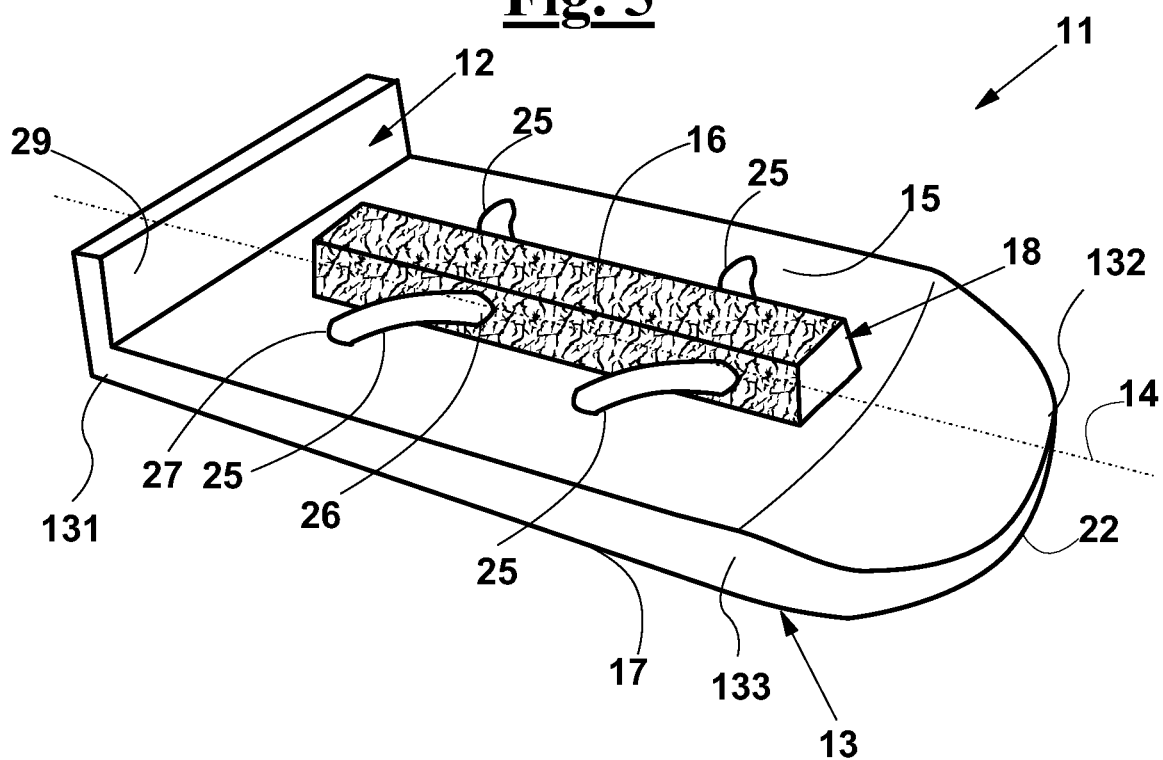
FIG. 5 shows a device according to an exemplary embodiment of the invention, in which the protrusion has a prismatic shape.

FIGS. 3 and 4 show devices 11, according to a first exemplary embodiment of the invention, for providing a partial endoprosthesis of a joint between two adjacent lower and upper vertebrae 10',10", wherein at least one of which is a cervical vertebra, in order to treat early articular painful conditions and early disc painful conditions in a patient, while preserving the relative mobility of two adjacent vertebrae 10',10". Device 11 is an one-side device, i.e. a device to be implanted between a couple of right or left adjacent articular facets 3',3", with respect to the mid-sagittal plane.

Device 11 comprises an articular portion 13 configured for introduction into articular space 7, i.e. between two upper 3' and lower 3" facets of lower 10' and upper 10" vertebra, respectively, as shown in FIGS. 1 and 2. To this purpose, the thickness of articular portion 13 is preferably set between 0.5 mm and 3.5 mm, more preferably, the thickness is set between 1 mm and 3 mm, even more preferably between 1 mm and 2 mm.

In FIG. 3, articular portion 13 is shown with a substantially rectangular shape, the sides thereof having length and width a,b, respectively, wherein both length a and width b, independently from each other, are set between 8 mm and 15 mm, in particular between 10 mm and 14 mm, more in particular, between 10 mm and 12 mm. However, articular portion 13 can have any shape, even a non-rectangular shape, which is preferably contained in a rectangle of sides a,b as described above.

However, articular portion 13 can have any shape, even a non-rectangular shape, that is preferably contained in a rectangle of sides a,b as described above. Preferably, as shown without limitation purpose in FIG. 4, articular portion 13 has a curved front end portion 132 so as to assist introduction of articular portion 13 into articular space 7. Moreover, as shown in FIGS. 4-8, the height of articular portion 13 can increase gradually from front end portion 132 to a maximum thickness portion 133.

In the pictures, the protrusion has a width k of about ⅕-¼ the width b of articular portion 13. However, more in general, although this is not shown, protrusion width k can be lower than 0.5b, and is preferably set between 0.1b and 0.4b.

Even if a single protrusion 18 is shown in the figures, the protrusion can be made as a plurality of separated portions arranged along the longitudinal axis of articular portion 13.

Articular portion 13 has a first face 15 with at least one part covered by an osteointegrable material 16. Osteointegrable material 16 is located on a central protrusion 18 whose height is set between 0.5 mm and 3 mm, preferably between 1.5 mm and 2.5 mm, and that is preferably oriented along a longitudinal axis 14 of articular portion 13.

According to the invention, beside protrusion 18 elongated and flexible primary stabilization elements 25 are provided laterally extending from protrusion 18. Primary stabilization elements 25 preferably extend along a plane parallel to a surface of first face 15. Primary stabilization elements 25 are arranged with an own free end 27 behind an own connection end 26 connected to protrusion 18. In other words, primary stabilization elements 25 and the direction of longitudinal axis 14 of articular portion 13 form an acute angle β, preferably set between 30° and 60° in an undeformed configuration of flexible elements 25, oriented towards first end 131 of articular portion 13.

Primary stabilization elements 25 can be substantially linear, as shown in FIG. 3, but preferably, in an undeformed configuration, they can be curved with respect to a line from connection end 26 to free end 27. In particular, in this case, primary stabilization elements 25 have a convexity oriented towards protrusion 18.

In an exemplary embodiment, not shown, free ends 27 of primary stabilization elements 25 can be provided with hooks.

Preferably, as shown in the figures, primary stabilization elements 20 are arranged symmetrically to longitudinal axis 14 of articular portion 13, however, although this is not shown, corresponding primary stabilization elements 20 on both sides of protrusion 18 can be shifted with respect to each other along the direction of longitudinal axis 14.

Device 11 also comprises a shoulder portion 12 configured to abut against one of laminae 4',4" of lower or upper vertebrae 10',10", in the case shown here against one of laminae 4" of upper vertebra 10". Abutment portion 12 is adjacent and arranged at an angle with respect to articular portion 13, and has an engagement face 29 that is oriented towards first face 15 of the articular portion and is configured to abut against one of laminae 4',4". Like articular portion 13, In this exemplary embodiment of FIG. 3, shoulder portion 12 has a substantially rectangular shape.

This way, once articular portion 13 has been inserted between upper 3' and lower 3" articular facets, shoulder portion 12 can abut against laminae 4' next to respective upper articular process 2" in order to avoid any further forward displacement into articular space 7, and to assist stabilization of device 11 in its implant location. This prevents dissemination of device 11 within the spine, as well as damages to spinal cord 38.

Central protrusion 18 can have any shape, provided it can have lateral elongated primary stabilization elements 25. For instance, central protrusion 18 can have a curvilinear cross section, for example a semicylindrical cross section, as in the exemplary embodiment of FIG. 4; as an alternative, it can have a prismatic shape, as in the exemplary embodiment of FIG. 5.

Even if the figures only show the preferred shapes, in which the protrusion has a substantially uniform height over the first face, the height can also change along the direction of longitudinal axis 14.

Figure 6:
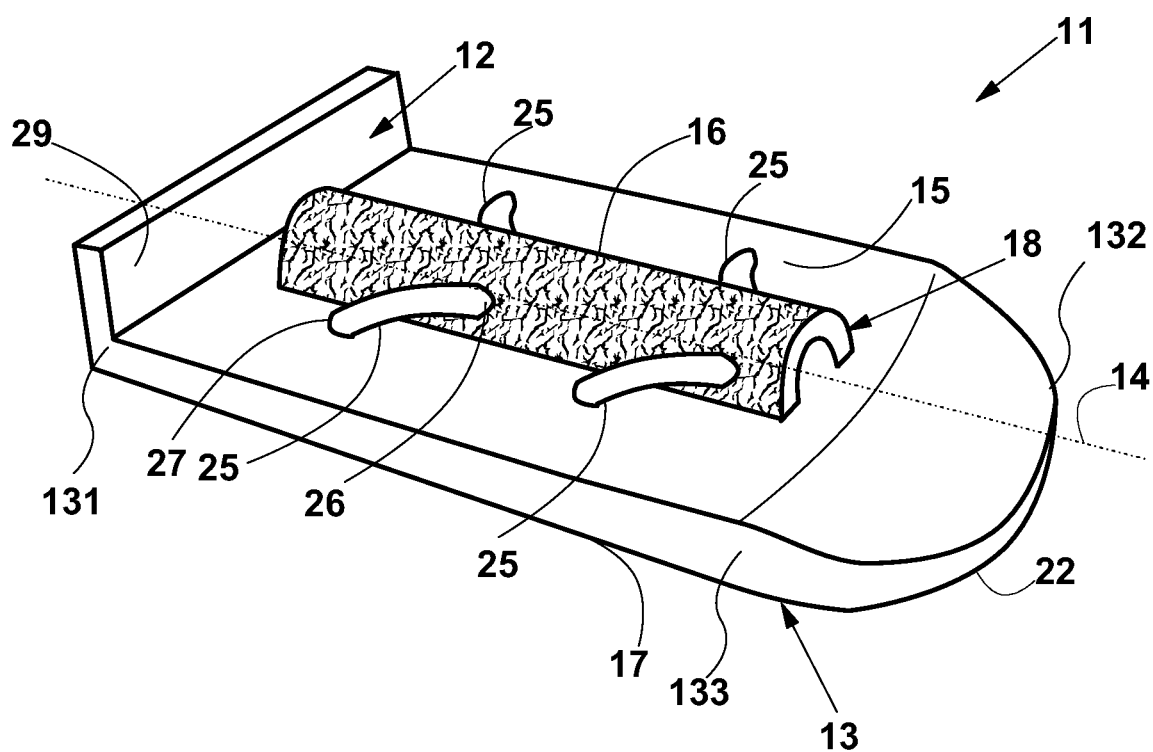
FIG. 6 shows a device according to an exemplary embodiment of the invention, in which the protrusion has a hollow structure.

Moreover, protrusion 18 can have a hollow structure, for example a shell structure or a box-like structure, as shown in the non-limiting cylindrical shape of FIG. 6. In this case, the hollow structure can be manufactured as a shell, i.e. it can have a curvilinear cross section, but in another exemplary embodiment, not shown, it can also have a box-like structure, i.e. it can have the shape of a hollow prism, in particular the shape of a hollow parallelepiped. In particular, a hollow structure of any shape can be integrally manufactured in an osteointegrable material, for example in a porous material.

An osteointegrable material such as bank bone can be introduced into the hollow structure, in order to assist osteointegration.

In exemplary device 11 configured as shown in FIG. 7, osteointegrable material 16 is not limited to the exposed surface of protrusion 18, but it is arranged on at least one part of first face 15, in particular it can be arranged on a region 19 close to protrusion 18 and, in particular, in an exemplary embodiment, not shown, it can be arranged all over first face 15 contacting the facet of FIG. 1, or it can be arranged on an area surrounding protrusion 18 only. In this case, protrusion 18 preferably extends from this further region 19.

In this case, the shell or box-like structure can extend from this further surface portion 19 of face 15 made of said osteointegrable material. Similarly, in an exemplary embodiment, not shown, osteosynthesis material 16 can optionally be present also on engagement face 29 of shoulder portion 12, besides first face 15 of articular portion 13.

In particular, device 11 can have a configuration obtained as a combination of the features of the devices shown in FIGS. 6 and 7.

As shown still in FIGS. 3 and 4, according to the invention, the thickness of articular portion 13, in a particular exemplary embodiment, increases from a value $s_1$ at a first end portion 131 thereof adjacent to shoulder portion 12, to a value $s_2 > s_1$ at a second end portion 132 thereof opposite to end portion 131 (FIG. 3), or at a maximum thickness portion 133 close to second end portion 132. In particular, thickness 52 at second end portion 132 or at maximum thickness portion 133 is higher than thickness $s_1$ of first end portion 131 by an amount set between 0.5 and 0.7 mm.

Osteosynthesis material 16, in any of the preferred above-mentioned exemplary embodiments, or in an exemplary embodiment obtained by combining the features thereof, can be made by a conventional surface treatment of a titanium or titanium alloy body forming articular portion 13, so as to obtain a porous or corrugated surface 15, in particular a surface having a roughness higher than 0.2 µm, in particular a roughness between 0.2 and 2 µm.

In an advantageous exemplary embodiment, the osteosynthesis material is trabecular titanium. As an alternative, osteosynthesis material 16 can be arranged on face 15 by laying thereon a layer of an osteosynthesis material like hydroxyapatite.

Moreover, still with reference to FIGS. 3-9, articular portion 13 has a smooth and regular second face 17, opposite to the first face. In particular, second face 17 has a surface roughness Ra lower than 0.2 µm or, advantageously, lower than 0.1 µm, preferably lower than 0.05 µm, more preferably surface roughness Ra is lower than 0.025 µm. This condition can be matched by a surface treatment of articular portion 13 that a skilled person can select among known treatments, such as a lapping or mirror polishing.

Also second face 17 can be made of Titanium. In this case, device 11 can be manufactured as a single piece, in which first face 15 has the above-mentioned corrugation and roughness, and the second face 17 is finished as indicated above.

As an alternative, second face 17 can even be made in a ceramic or glass material, provided it has the above-mentioned finishing and compression strength. In this case, device 11 can be manufactured in two parts, with a layer of ceramic or glass material arranged on a metal support such as a titanium support, which provides first face 15 of device 11.

Device 11 can be made of a single material, such as titanium or a biocompatible and osteointegrable alloy thereof, provided first face 15 has the above-mentioned roughness or porosity, and second face 17 is suitably smooth, i.e. it is finished as specified above.

As an alternative, device 11 can comprise two materials, for example a biocompatible base material, such as titanium or a surgical steel or also a ceramic or plastic material such as PEEK, and an osteosynthesis material 16 present at least on protrusion 18 of first face 15, such as a hydroxyapatite layer.

Briefly, first face 15 is configured to integrate by osteosynthesis with the surface of one of mutually articulated two facets 3',3", in particular at protrusion 18, in this case with lower facet 3" of upper vertebra 10", in a secondary stabilization process of device 11. This occurs after at least partial removal of natural connective tissue from articular space 7 and, once the cartilage has been removed, after cruentation of the surface of facet 3", preferably by removing a portion of cortical bone therefrom.

On the other hand, face 17, is configured in order to slide with negligible friction on the surface of the other of mutually articulated two facets 3',3", in this case on the surface of upper facet 3' of lower vertebra 10', in the same way as the surface of facet 3" slides on facet 3' in a natural joint, through the connective tissue, in particular in a rotation movement of adjacent vertebrae 10' and 10" with respect to each other.

Therefore, device 11 is configured to integrate with one of two lower and upper vertebrae 10',10", in particular with upper vertebra 10", by an osteointegration process, and to slide on facet 3' of the joint comprising two facets 3',3". Even if the drawings show first osteointegrable surface 15 of portion interarticular 13 arranged to replace the lower bone joint surface 3" of upper vertebra 10", and low-friction second face 17 is arranged to slide on upper bone joint surface 3' of lower vertebra 10', the device can be manufactured in such a way to arrange first surface 15 to replace upper bone joint surface 3' of lower vertebra 10', and second face 17 to slide on the lower bone joint surface 3" of upper vertebra 10".

Device 11 can indifferently be used on the right side or on the left side with respect to the patient's mid-sagittal plane. Advantageously, device 11 can be provided as a couple of devices, to provide bilateral partial endoprosthesis between two adjacent vertebrae.

The foregoing description exemplary specific embodiments of the invention will so fully reveal the invention according to the conceptual point of view, so that others, by applying current knowledge, will be able to modify and/or adapt in various applications the specific exemplary embodiments without further research and without parting from the invention, and, accordingly, it is meant that such adaptations and modifications will have to be considered as equivalent to the specific embodiments. The means and the materials to realize the different functions described herein could have a different nature without, for this reason, departing from the field of the invention. It is to be understood that the phraseology or terminology that is employed herein is for the purpose of description and not of limitation.

The invention claimed is:

1. A partial endoprosthesis device for preserving the motion of a vertebral joint for implant into a spinal segment comprising two adjacent vertebrae, wherein at least one of said two adjacent vertebrae is a cervical vertebra, said adjacent vertebrae including a lower vertebra having a couple of upper articular processes with respective upper articular facets and an upper vertebra-having a couple of lower articular processes with respective lower articular facets, each upper articular facet of said lower vertebra articulated with a corresponding lower articular facet of said upper vertebra, said device comprising:

an elongated articular portion extending along a longitudinal axis between a first end and a second end axially opposite to each other, said articular portion having a first face and a second face opposite to said first face, wherein:

said first face includes a central protrusion along said longitudinal axis that has a height (H), with respect to said face, set between 0.5 mm and 3 mm, and that exposes an osteointegrable material, wherein said first face has a plurality of primary stabilization elements, wherein said second face has a surface roughness Ra lower than 0.2 µm, a shoulder portion adjacent to said first end and arranged at an angle with respect to said articular portion opposite to said second face;

said articular portion has a thickness increasing from said first end going towards said second end, and said primary stabilization elements are elongated and flexible elements, and each primary stabilization elements extends laterally with respect to said protrusion, between a first connection end of said primary stabilization element, for connecting with said protrusion, and a free end of said primary stabilization element, and form an acute angle with a direction of said longitudinal axis of said articular portion, said acute angle oriented towards said first end of said articular portion, in order to fasten said articular portion to said first face.

2. The partial endoprosthesis device according to claim 1, wherein said acute angle, in a undeformed configuration, is set between 30° and 60°.

3. The partial endoprosthesis device according to claim 1, wherein said primary stabilization elements, in an undeformed configuration, have a curvature with respect to a line between said connection end and said free end.

4. The partial endoprosthesis device according to claim 1, wherein said primary stabilization elements are arranged symmetrically with respect to said longitudinal axis of said articular portion.

5. The partial endoprosthesis device according to claim 1, wherein said surface roughness of said second face is lower than 0.1 µm.

6. The partial endoprosthesis device according to claim 1, wherein said protrusion has a substantially uniform height (Q) over said first face.

7. The partial endoprosthesis device according to claim 1, wherein said protrusion has a shape selected from the group consisting of:
a semicylindrical shape; and
a prismatic shape.

8. The partial endoprosthesis device according to claim 1, wherein said protrusion is a hollow protrusion.

9. The partial endoprosthesis device according to claim 1, wherein said first face comprises a further osteointegrable material adjacent to said protrusion.

10. The partial endoprosthesis device according to claim 9, wherein said further osteointegrable material is selected from the group consisting of:
a porous osteointegrable material;
and
an osteointegrable material having a surface roughness Ra higher than 0.2 µm.

11. The partial endoprosthesis device according to claim 9, wherein said osteointegrable material comprises trabecular titanium.

12. The partial endoprosthesis device according to claim 1, wherein said thickness of said articular portion is set between 0.5 mm and 3.5 mm.

13. The partial endoprosthesis device according to claim 1, wherein said thickness of said articular portion at a maximum thickness portion is higher than said thickness (s1) at said first end by an amount set between 0.5 and 0.7 mm.

14. The partial endoprosthesis device according to claim 1, wherein said articular portion has a maximum length, along said longitudinal axis, and a maximum width, transversally to said longitudinal axis, independently from each other, set between 8 mm and 15 mm.

15. The partial endoprosthesis device according to claim 14, wherein said articular portion has a rectangular shape with sides equal to respectively, said maximum length and said maximum width.

16. The partial endoprosthesis device according to claim 1, wherein said articular portion has a width, transversally to said longitudinal axis, and said protrusion has a width, transversally to said longitudinal axis shorter than one half of said width.

17. The partial endoprosthesis device according to claim 1, wherein said shoulder portion has fastening means for fastening a percutaneous positioning device.

18. The partial endoprosthesis device according to claim 1, wherein said osteointegrable material of said central protrusion is selected from the group consisting of:
a porous osteointegrable material;
and
an osteointegrable material having a surface roughness Ra higher than 0.2 µm.

19. The partial endoprosthesis device according to claim 1, wherein said osteointegrable material comprises trabecular titanium.

* * * * *